United States Patent
Kuo (10) Patent No.: US 10,385,378 B2
(45) Date of Patent: Aug. 20, 2019

(54) METHOD FOR DETERMINING TOXIC SUBSTANCES BY PLANT GEL AGAR COAGULATION

(71) Applicant: Chun-Cheng Kuo, Tainan (TW)

(72) Inventor: Chun-Cheng Kuo, Tainan (TW)

( * ) Notice: Subject to any disclaimer, the term of this patent is extended or adjusted under 35 U.S.C. 154(b) by 0 days.

(21) Appl. No.: 15/655,209

(22) Filed: Jul. 20, 2017

(65) Prior Publication Data
US 2019/0024134 A1    Jan. 24, 2019

(51) Int. Cl.
*C12Q 1/02* (2006.01)
*C12R 1/89* (2006.01)

(52) U.S. Cl.
CPC .............. *C12Q 1/025* (2013.01); *C12R 1/89* (2013.01); *G01N 2333/405* (2013.01)

(58) Field of Classification Search
None
See application file for complete search history.

(56) References Cited

PUBLICATIONS

Material Safety Data Sheet: Ethanolamine, Acros Organics, Jul. 15, 2011 (Year: 2011).*
Material Safety Data Sheet: Lactic acid, Sciencelab.com, Oct. 9, 2013 (Year: 2013).*
Material Safety Data Sheet: Ammonium lauryl sulfate, Colonial Chemical Inc, May, 1, 2014 (Year: 2014).*

* cited by examiner

*Primary Examiner* — David W Berke-Schlessel
(74) *Attorney, Agent, or Firm* — Rosenberg, Klein & Lee (57) ABSTRACT

The present invention relates to a method for rapid detection of toxicity comprising the steps of: preparing a plant gel agar and a sample under study, mixing the agar gel with the sample under study to form a mixture, and measuring a coagulation time of the mixture to determine cytotoxicity of the sample under study.

7 Claims, 6 Drawing Sheets

METHOD FOR DETERMINING TOXIC SUBSTANCES BY PLANT GEL AGAR COAGULATION

FIELD OF THE INVENTION

The present invention relates to a method for rapid determination of a toxic substance, and in particular, to a method using a plant gel agar coagulation for determining whether a sample is toxic. This method can reduce the use of animal or cell experiments for the purpose of protecting animals, and also for reducing the cost of the toxicity test of drugs, food or cosmetics.

BACKGROUND OF THE INVENTION

According to the existing domestic and foreign regulations, for the health safety, food products, new raw materials, drug-containing cosmetics, medical equipment and pharmaceuticals are required to be exposed to different toxicological assessments of raw materials which may involve acute toxicity experiments, eye irritation experiments, skin irritation experiments, etc. The aforementioned experiments are expensive because they often require experiments on animals, and thus, the lives of numerous animals may be sacrificed during such experiments.

In addition, the EU has banned the use of animals for cosmetics testing since March 2009. EU regulations for cosmetics sales have been more regulated since 2013 to prohibit the use of animals for toxic safety experiments of cosmetics. Cosmetics companies and academic organizations are actively engaged in non-animal safety testing methods for cosmetics toxicity. Currently used methods mainly focus on cytotoxicity testing as a cosmetic safety indicator.

Although animals are not used in the cosmetic toxicity safety tests based on cytotoxicity, culture cells used in cytotoxicity testing require to use a large amount of serum and to consume an excessive amount of time to analyze the toxicity test results. Generally, the research and development costs for the toxicity safety texting are excessive for most manufacturers.

Accordingly, it is a long-lasting need to develop a simple and rapid toxicity test method for reducing use of animals in the toxicity tests and to improve the cytotoxicity safety testing.

SUMMARY OF THE INVENTION

In general, a term "gelation" refers to the branching of macromolecular chains that form a non-liquid colloid through a gradually increasing branching process, which depends on the structure and conformation of the starting material. Such polymer materials are known as "sol" due to the presence of the multi-branched water-soluble branch.

A term "infinite polymerization structure" is referred to as a "gel" or "network", because the gelation link process is accompanied by a gradual increase in the size of the branched polymer and decrease in solubility.

The transition from a limited branched polymer to an infinite polymeric structure is referred to as a "sol-gel transition" (or "gelation"). Different types of the gelation mechanism can be generated by physical linking (physical gelation) or by chemical attachment (chemical gelation). The physical hydrogel is formed by the intermolecular electrostatic force (ionic action), hydrogen bond and hydrophobic interaction, characterized by the reversibility property.

In view of the above, the present invention provides a rapid and simple method for the determining a presence of toxic substances by measuring coagulation time of plant gel agar to determine whether the sample affects the chemical bond, and further determining whether the sample has a biological toxicity. In the subject method, the use of animals or cell experiments can be reduced, not only for the purpose of protecting animals and for reducing the cost of toxicological safety tests for drugs, food products, and cosmetics.

The present invention provides a rapid and simple method for determining toxic substances based on a plant gel agar coagulation, which includes:

Step 1: preparing an agar and a sample under study, and heating the agar to be completely dissolved to form a hot agar solution;

Step 2: mixing the hot agar solution and the sample under study in a carrier to form a mixture; and Step 3: cooling the mixture at a room temperature to 25° C. during a time duration, wherein the time duration is the coagulation time of the agar, wherein the coagulation time of 15 minutes is used to determine the cytotoxicity of the sample.

The agar concentration of the hot agar solution preferably ranges between 1% and 6% (w/w). The volume of the hot agar solution ranges between 1 mL and 250 mL.

When the coagulation time is greater than 15 minutes, the sample under study is classified as a toxic substance; and when the coagulation time is below than 15 minutes, the sample is classified as not a non-toxic substance.

The term "irritation" is defined as the destruction of a cell membrane, cytoplasm, and organism, resulting in the cell disintegration and necrosis. This disintegration and necrosis are usually related to the destruction of the whole cell structure caused by foreign matter, such as a structural damage to the constituent cytochemical composition.

In one embodiment of the present invention, the plant gel material is selected from agar.

Preferably, in one embodiment of the invention, the sample may be, for example, a drug, a food, or a cosmetic.

Cell is the smallest unit of an organism. Cells contain a variety of life molecules formed by a variety of chemical bonding compositions. In the present method, observation of life molecules disintegration as the degree of injury can be replaced by observation of the degree of chemical bond damage to be used as a toxicity indicator.

Thus, the subject method can quickly detect whether the sample under study is a toxic substance that affects cells or organisms. Even though the toxic substance is difficult to pass through the cell membrane or the cytotoxicity can be detected by a lengthy observation in conventional method, it is detectable by the method of present invention which overcomes the shortcomings of the conventional methods. The method of the present invention does not require the use of cells (as in the cytotoxicity tests) or animal experiments, thereby significantly reducing the cost of toxicity testing.

The present invention can be applied to the clinical trial design and management system, the IRB review operating system, the information system of the contract research institution (CRO), etc., which can support designing the clinical trial protocols under the regulation of clinical trial review unit Good Clinical Practice (GCP).

DETAILED DESCRIPTION OF THE INVENTION

The present invention was tested for different concentrations or different contents of cosmetic materials (samples under study). In the subject method, the cosmetic raw materials (samples) were selected from the group consisting of Ammonium Lauryl Sulfate, Butyl Paraben, Disodium Lauroamphodiacetate, Monoethanolamine, Glycerin, Hydrogen Peroxide, Hydroxy Ethyl Cellulose, Lysine hydrochloride, methyl p-hydroxybenzoate, Methylchloroisothiazolinone, Butylene glycol, p-Methylaminophenol Sulfate, Polyethylene Glycol, Polyquaternium-7, p-phenylenediamine Resorcinol, Salicylic Acid, 2-Aminophenol, 3-Aminophenol, Sodium Sulfide-9-Hydrate Squalane, Tocopherol Acetate, Trisodium Citrate Dihydrate, Isopropyl Myristate, and Lactic Acid.

In one of the embodiment of the present invention, the plant gel material is selected from agar.

In one embodiment, the present invention is applicable for testing of a sample under study, which, for example, includes, but is not limited to, a drug, a food, or a cosmetic.

The agar concentration used in the present method is, for example (but not limited to), 1%, 2%, 3%, 4%, 5%, and 6%. (w/w).

The agar volume of used in the present method ranges from 1 ml (mL) to 250 ml (mL) and may be, for example (but not limited to), 1 ml, 2 ml, 3 ml, 4 ml, 5 ml, 6 ml, 7 ml, 8 ml, 9 ml, 10 ml, 50 ml, 100 ml, 150 ml, 200 ml, and 250 ml.

The coagulation time of the plant gel used in the present method, is in particular the coagulation time of the agar gel.

The agar gel solution is dissolved to form a clear solution by changing the temperature in the range from a room temperature to 25° C. The agar gel solution is held in a carrier, such as a bottle, or a test tube, and is tilted at about 30°-60° (for example, 45°) from the vertical orientation. The coagulation time is defined when the agar gel solution ceases to flow.

Figure 1:
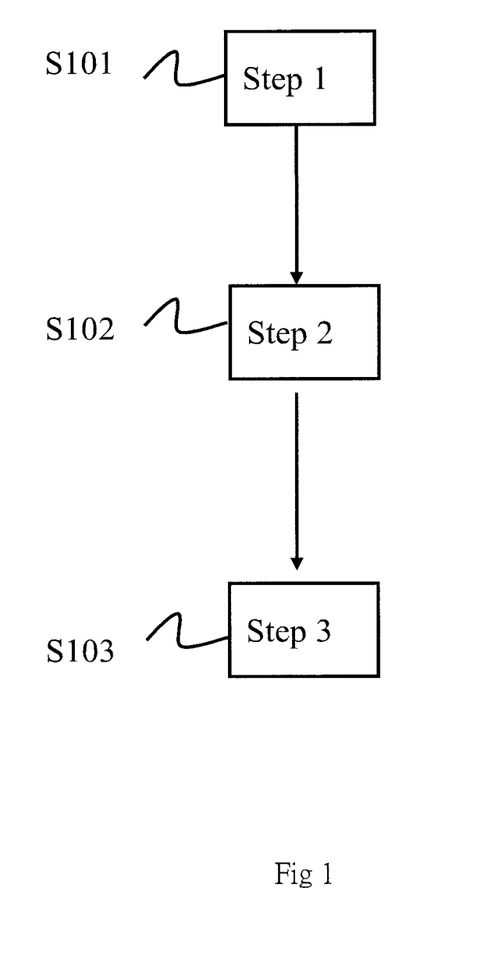
FIG. 1 is a flow chart of the preferred embodiment of the subject method steps.

Referring to FIG. 1, the present invention relates to a method for rapid determination of toxicity of a substance, and in particular, to a method for determining whether a sample under study is toxic based on a plant gel agar coagulation. The subject method includes the following steps:

Step 1 (S101): preparing a plant gel material and a sample under study.

Step 2 (S102): mixing the plant gel material and the sample under studyU to form a mixture.

Step 3 (S103): measuring the coagulation time of the mixture.

According to the present invention, the change of the gel bonding coincides with the damage of the living tissue and/or the cell structure caused by the toxic sample. The biological toxicity of the sample under study and the irritation to the living tissue are defined by the coagulation time of the plant gel agar.

The term "irritation" is defined as the destruction of a cell membrane, cytoplasm, and organogenesis, which is usually disintegrated and necrotic. This disintegration/necrosis is usually related to the destruction of the whole cell structure caused by a foreign matter, for example, with the constituent cytochemical composition bonding damage related. In other words, the "irritation" in the present invention method may be derived from a cell viability and cytotoxicity assays.

The scope of the present invention may be further illustrated by the following specific examples, which are not intended to limit the scope of the invention in any way.

Example 1: Cell Viability Analysis

The B16-F10 cells (purchased from the Food Industry Development Institute Fellowship Center/National Institutes of Health Cell Bank, ATCC number: CRL-6475) and skin 3T3 cells (purchased from the Food Industry Development Institute Center/National Institutes of Health Cell Bank, ATCC number: CCL-92) were purchased to test the toxicity of each sample (IC50: µg/ml).

The MTT reagent was reduced to the purple crystalline formazan by the mitochondrial enzyme of surviving cells, and the crystals were dissolved by DMSO (Dimethyl Sulfoxide).

Subsequently, the absorbance of OD570 nm was measured. The color depth was proportional with the number of viable cells. Skin B16-F10 cells and skin 3T3 cells were seeded in 96-well plates with $8 \times 10^3$ per well. After 3-5 hours, the cells were plated on 96-well plates and added to the sample (100 µl per well). After incubation for 24 hours, the MTT reagent (MTT 5 mg/ml dissolved in PBS) was reacted for 1 to 2 hours. The culture medium in the 96-well dish was blotted with the MTT reagent and dissolved in 100 µl of DMSO. The absorbance values were read at a wavelength of 570 nm with an ELISA kit.

The term IC50 refers to a half of the concentration of a drug or substance (inhibitor) that inhibits certain biological procedures (or some of the substances used in the procedure, such as enzymes, cell receptors, or microorganisms), such as enzymatic reaction, or antigen-antibody reaction. In the cytotoxicity test, a specific concentration of a drug cause the cell death by 50% is called 50% inhibition concentration. That means, that the ratio of the dead cells to all cells is equal to 50% of the corresponding concentration IC50 value, which can be used to measure the death inducing ability of drugs, that is, the a stronger the ability of the aforementioned drugs to induce death, corresponds to a lower the value of the ratio.

The present method obtains data using the cytotoxicity IC50 of various cosmetics materials by cell survival analysis, which can be compared with the coagulation time of various cosmetic materials in the different embodiments described in further paragraphs.

Example 2: Evaluate the Effect of Various Cosmetic Materials on Agar Coagulation Time Agar is extracted from a seaweed. Its polysaccharide body is closely related to the formation of the hydrogen bond during the cooling and coagulation. The subject method utilizes a carrier (such as, for example, a test tube) to observe the effect of added cosmetic material to the coagulation of agar, so as to assess the toxicity of cosmetic materials. In this example, the present invention further evaluates the relevance of the cosmetic material toxicity based on the agar coagulation time with the cytotoxic IC50 testing.

The agar was prepared to be used as the main application material (the plant gel material) for the present invention, and a sample was prepared to test the coagulation time of the agar (for 25 samples under study) as described above. For example, the concentrations of agar solutions are 1%, 2%, 3%, 4%, 5%, and 6% (w/w). In one of the examples, 3% agar solution was heated to 100° C. to be dissolved, and then 100 ml or 200 ml of agar solution was added to a bottle or a test tube to be mixed with various samples (100 ml, or 200 ml). The bottle, or the test tube, were tilted about 45° relative to a plane each 30 seconds, to observe whether there is coagulation, and the cooling from 100° C. to room temperature and corresponding coagulation times were recorded.

The term Equivalence is defined as a Number of Compounds Correctly Identified/Total Number of Compounds Tested.

The Sensitivity is defined as a Number of Irritants Correctly Identified/Total Number of Irritants (samples of irritated samples/all irritating samples).

The Specificity is defined as a Number of Non-Irritants Correctly Identified/Total Number of Non-Irritants (all non-irritating samples/all non-irritating samples).

The False positive rate is defined as a Number of Non-Irritants Classified as Irritants/Total Number of Compounds Tested (no irritating sample is detected as irritant/all samples).

The False Negative Rate is defined as a Number of Irritants Classified as Non-Irritants/Total Number of Compounds Tested (irritated samples are measured as non-irritating/all samples).

TABLE 1

The relevance of the cosmetic material based on agar coagulation time and the cytotoxic IC50

| Parameters 1 | B16-F10 | 3T3 |
| --- | --- | --- |
| Equivalence (%) | 92.0 (23/25) | 92.0 (23/25) |
| Sensitivity (%) | 100 (9/9) | 100 (8/8) |
| Specificity (%) | 87.5 (14/16) | 82.35 (14/17) |
| The False positive rate (%) | 0 (0/25) | 0 (0/25) |
| False Negative Rate (%) | 8.0 (2/25) | 12 (3/25) |

The Parameters 1 in Table 1 refer to the classification of samples with 5% (w/w) concentration. When the cosmetic material at is tested with 3% agar, the coagulation time greater than 15 minutes is used as the determination point of toxicity (cytotoxicity IC50 less than 250 µg/ml).

TABLE 2

The effect of cosmetic materials based on the coagulation time of agar and cytotoxicity (1)

| Name 1 | concentration % (w/w) | Agar coagulation time (min) | B16-F10 cytotoxicity $IC_{50}$: µg/ml | Skin cell 3T3 Cytotoxicity $IC_{50}$: µg/ml |
| --- | --- | --- | --- | --- |
| AmmoniumLauryl Sulfate | 0 | 13.234 ± 0.188 | 53.7 | 57 |
| | 1 | 16.444 ± 0.477 | | |
| | 5 | 18.811 ± 0.987 | | |
| | 10 | 28.372 ± 1.287 | | |
| | 15 | 39.572 ± 1.077 | | |
| Disodium Lauroamphodiacetate | 0 | 13.234 ± 0.188 | 72.8 | 55.6 |
| | 1 | 14.356 ± 0.097 | | |
| | 5 | 20.422 ± 0.106 | | |
| | 10 | 43.333 ± 0.112 | | |
| | 15 | 87.784 ± 0.176 | | |
| Hydrogen Peroxide | 0 | 13.234 ± 0.188 | 48.9 | 63.7 |
| | 1 | 18.406 ± 0.121 | | |
| | 5 | 30.544 ± 0.139 | | |
| | 10 | 91.139 ± 0.257 | | |
| | 17.5 | >1440 | | |
| Methylchloroisothiazolinone | 0 | 13.234 ± 0.188 | 58 | 36.5 |
| | 0.5 | 47.582 ± 0.103 | | |
| | 1 | 97.514 ± 0.103 | | |
| | 5 | 420.550 ± 0.073 | | |
| | 7 | >1440 | | |
| p-Methylaminophenol Sulfate | 0 | 13.234 ± 0.188 | 2.46 | 2.93 |
| | 1 | 15.478 ± 0.320 | | |
| | 5 | 21.428 ± 0.887 | | |
| | 10 | 32.489 ± 0.792 | | |
| | 20 | 56.917 ± 0.932 | | |
| | 30 | 88.311 ± 2.173 | | |
| p-Phenylenediamine | 0 | 13.234 ± 0.188 | 29.9 | 89.6 |
| | 1 | 16.245 ± 0.468 | | |
| | 5 | 22.189 ± 0.782 | | |
| | 10 | 27.500 ± 1.073 | | |
| | 20 | 39.489 ± 1.572 | | |
| | 30 | 52.689 ± 1.982 | | |

TABLE 2-continued

The effect of cosmetic materials based on the coagulation time of agar and cytotoxicity (1)

| Name 1 | concentration % (w/w) | Agar coagulation time (min) | B16-F10 cytotoxicity $IC_{50}$: μg/ml | Skin cell 3T3 Cytotoxicity $IC_{50}$: μg/ml |
|---|---|---|---|---|
| Resorcinol | 0 | 13.234 ± 0.188 | 4929.1 | 9858.2 |
| | 1 | 32.821 ± 0.082 | | |
| | 5 | 238.511 ± 0.101 | | |
| | 10 | >4320 | | |
| | 20 | >4320 | | |
| | 30 | >4320 | | |
| 2-Aminophenol | 0 | 13.234 ± 0.188 | 39.34 | 41.2 |
| | 1 | 15.231 ± 0.196 | | |
| | 5 | 20.35 ± 0.678 | | |
| | 10 | 29.44 ± 1.082 | | |
| | 20 | 44.339 ± 0.972 | | |
| | 30 | 61.421 ± 1.362 | | |
| 3-Aminophenol | 0 | 13.234 ± 0.188 | 126.5 | 307.8 |
| | 1 | 16.489 ± 0.475 | | |
| | 5 | 20.455 ± 0.968 | | |
| | 10 | 24.478 ± 1.280 | | |
| | 20 | 43.671 ± 0.886 | | |
| | 30 | 67.444 ± 1.687 | | |
| sodium Sulfide-9-Hydrate | 0 | 13.234 ± 0.188 | 4187.1 | >10000 |
| | 0.5 | 109.250 ± 0.101 | | |
| | 1 | >1440 | | |
| | 5 | >1440 | | |
| | 10 | >1440 | | |
| | 20 | >1440 | | |
| | 30 | >1440 | | |
| Lactic acid | 0 | 13.234 ± 0.188 | 66 | 30.483 |
| | 1 | 18.299 ± 0.078 | | |
| | 5 | 23.378 ± 0.091 | | |
| | 10 | 43.302 ± 0.099 | | |
| | 20 | 253.306 ± 0.124 | | |
| | 30 | >1440 | | |

The names in Table 2 above refer to the samples and cosmetics for which the agar coagulation time is greater than 15 minutes when the concentration (w/w) is 5%.

TABLE 3

The effect of cosmetic materials on the coagulation time of agar and cytotoxicity (2)

| Name 2 | concentration % (w/w) | Agar coagulation time (min) | B16-F10 cytotoxicity $IC_{50}$: μg/ml | Skin cell 3T3 Cytotoxicity $IC_{50}$: μg/ml |
|---|---|---|---|---|
| Butyl Paraben | 0 | 13.234 ± 0.188 | >10000 | 3564.7 |
| | 1 | 13.186 ± 0.080 | | |
| | 5 | 13.210 ± 0.079 | | |
| | 10 | 13.182 ± 0.076 | | |
| | 20 | 13.141 ± 0.050 | | |
| | 30 | 13.238 ± 0.107 | | |
| Monoethanolamine | 0 | 13.234 ± 0.188 | 3646.4 | >10000 |
| | 1 | 13.193 ± 0.067 | | |
| | 5 | 13.251 ± 0.077 | | |
| | 10 | 13.296 ± 0.066 | | |
| | 20 | 13.345 ± 0.088 | | |
| | 30 | 13.354 ± 0.083 | | |
| Glycerin | 0 | 13.234 ± 0.188 | >10000 | >10000 |
| | 1 | 13.220 ± 0.081 | | |
| | 5 | 13.228 ± 0.053 | | |
| | 10 | 13.333 ± 0.087 | | |
| | 20 | 13.265 ± 0.067 | | |
| | 30 | 13.322 ± 0.091 | | |
| Hydroxy Ethyl Cellulose | 0 | 13.234 ± 0.188 | >10000 | 4207.8 |
| | 1 | 13.17 ± 0.060 | | |
| | 5 | 13.216 ± 0.089 | | |
| | 10 | 13.216 ± 0.087 | | |
| | 20 | 13.193 ± 0.064 | | |
| | 30 | 13.219 ± 0.093 | | |

TABLE 3-continued

The effect of cosmetic materials on the coagulation time of agar and cytotoxicity (2)

| Name 2 | concentration % (w/w) | Agar coagulation time (min) | B16-F10 cytotoxicity $IC_{50}$: μg/ml | Skin cell 3T3 Cytotoxicity $IC_{50}$: μg/ml |
|---|---|---|---|---|
| Lysine hydrochloride | 0 | 13.234 ± 0.188 | 4377.3 | >10000 |
| | 1 | 13.241 ± 0.080 | | |
| | 5 | 13.198 ± 0.077 | | |
| | 10 | 13.238 ± 0.100 | | |
| | 20 | 13.254 ± 0.119 | | |
| | 30 | 13.286 ± 0.147 | | |
| methyl p-hydroxybenzate | 0 | 13.234 ± 0.188 | 4853.9 | >10000 |
| | 1 | 13.230 ± 0.084 | | |
| | 5 | 13.197 ± 0.066 | | |
| | 10 | 13.242 ± 0.087 | | |
| | 20 | 13.208 ± 0.100 | | |
| | 30 | 13.203 ± 0.090 | | |
| Butylene Glycol | 0 | 13.234 ± 0.188 | >10000 | 7323.7 |
| | 1 | 13.252 ± 0.100 | | |
| | 5 | 13.304 ± 0.077 | | |
| | 10 | 14.489 ± 0.082 | | |
| | 20 | 15.539 ± 0.101 | | |
| | 30 | 15.688 ± 0.088 | | |
| Polyethylene Glycol | 0 | 13.234 ± 0.188 | >10000 | >10000 |
| | 1 | 13.194 ± 0.077 | | |
| | 5 | 13.221 ± 0.091 | | |
| | 10 | 13.249 ± 0.098 | | |
| | 20 | 13.160 ± 0.072 | | |
| | 30 | 13.210 ± 0.072 | | |
| Polyquaternium-7 | 0 | 13.234 ± 0.188 | >10000 | >10000 |
| | 1 | 13.213 ± 0.081 | | |
| | 5 | 13.229 ± 0.070 | | |
| Salicylic Acid | 0 | 13.234 ± 0.188 | 413.7 | 1388.2 |
| | 1 | 13.210 ± 0.087 | | |
| | 5 | 13.221 ± 0.091 | | |
| | 10 | 13.144 ± 0.068 | | |
| | 20 | 13.219 ± 0.093 | | |
| | 30 | 13.184 ± 0.063 | | |
| Squalane | 0 | 13.234 ± 0.188 | 5423.2 | >10000 |
| | 1 | 13.260 ± 0.068 | | |
| | 5 | 13.199 ± 0.073 | | |
| | 10 | 13.276 ± 0.081 | | |
| | 20 | 13.254 ± 0.077 | | |
| | 30 | 13.305 ± 0.097 | | |
| Tocopherol Acetate | 0 | 13.234 ± 0.188 | >10000 | >10000 |
| | 1 | 13.200 ± 0.080 | | |
| | 5 | 13.209 ± 0.079 | | |
| | 10 | 13.185 ± 0.072 | | |
| | 20 | 13.167 ± 0.066 | | |
| | 30 | 13.192 ± 0.071 | | |
| Trisodium Citrate Dihydrate | 0 | 13.234 ± 0.188 | 3335.4 | >10000 |
| | 1 | 13.122 ± 0.020 | | |
| | 5 | 13.194 ± 0.048 | | |
| | 10 | 13.185 ± 0.048 | | |
| | 20 | 13.24 ± 0.069 | | |
| | 30 | 13.246 ± 0.072 | | |
| Isopropyl Myristate | 0 | 13.234 ± 0.188 | >10000 | >10000 |
| | 1 | 13.153 ± 0.056 | | |
| | 5 | 13.186 ± 0.069 | | |
| | 10 | 13.185 ± 0.066 | | |
| | 20 | 13.172 ± 0.065 | | |
| | 30 | 13.206 ± 0.087 | | |

The names in Table 3 above refer to the non-toxic samples and cosmetics for which the agar coagulation time is less than 15 minutes when the concentration (w/w) is 5%.

Figure 2:
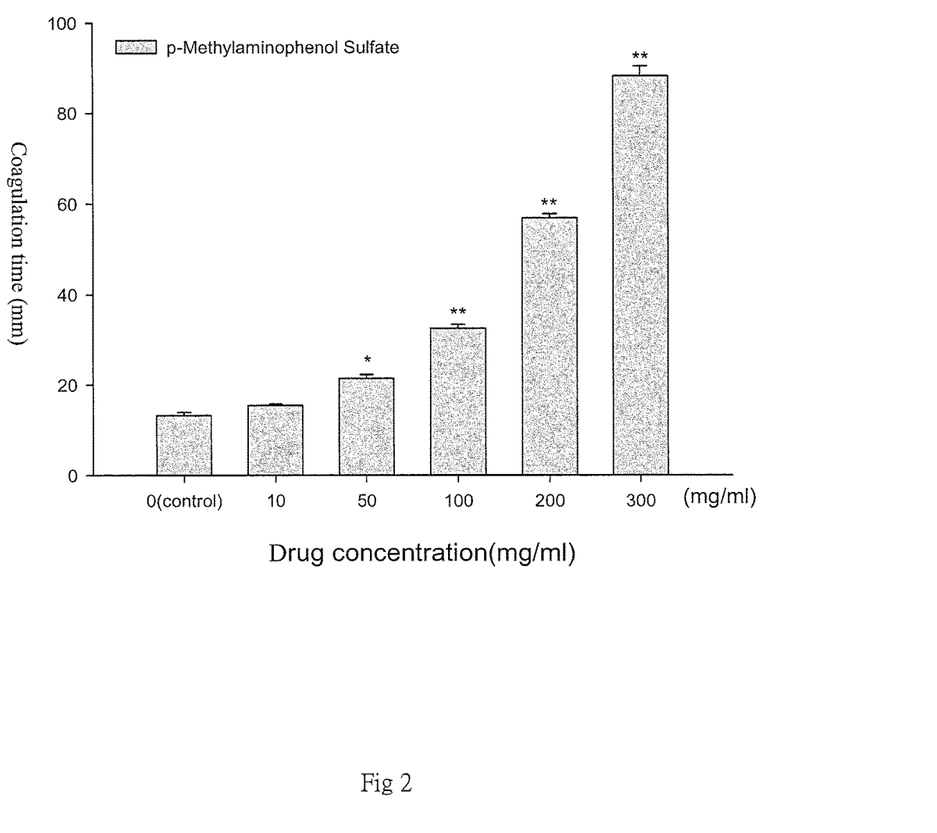
FIG. 2 is a diagram representative of the results of an analysis for different concentrations of p-methylaminophenol sulfate and coagulation time according to the present invention. As shown, p-Methylaminophenol Sulfate concentration increases the agglomeration time of agarose gel. In the presented diagram, the 0 group is the control group without adding the p-Methylaminophenol Sulfate.

In addition, the present invention also relies on the concentration-dependent relationship for the agar coagulation time for various cosmetic materials of different concentrations. FIG. 2 shows different agar coagulation with different types of cosmetics samples under study. With the increase of the concentration of p-Methylaminophenol Sulfate, the agar coagulation time is significantly longer and statistically significant. "*" represents the control group p<0.05 compared to the control group p<0.05; "**" represents the control group p<0.01 compared to the control group p<0.05). The data is expressed in mean±SEM for the triple test shown in FIG. 2; Data are represented as the mean±SEM; N=3○*p<0.05 compared with the control group; **p<0.01 compared with the control group.

Figure 3:
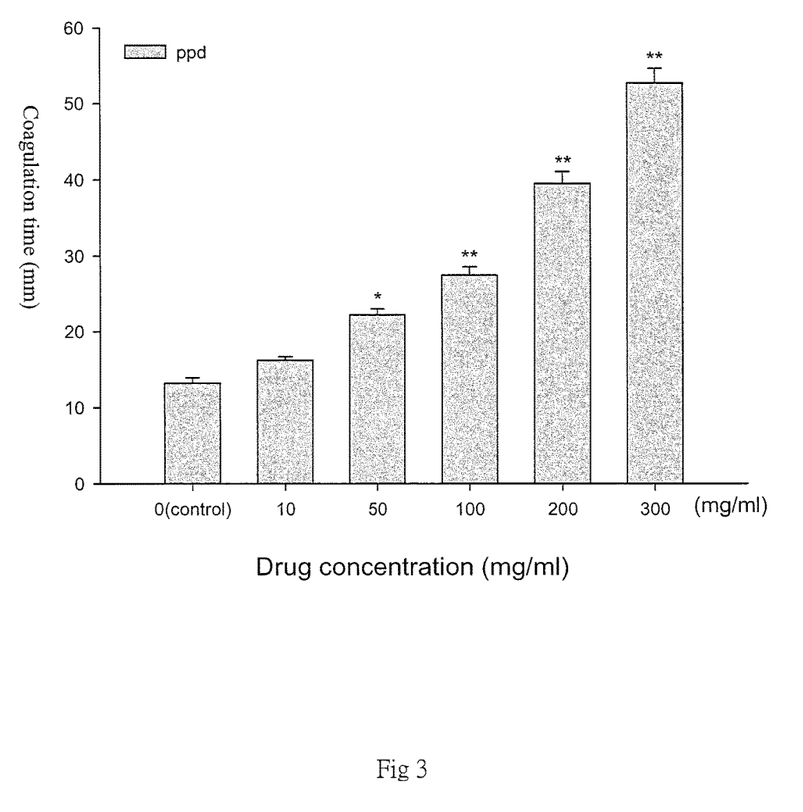
FIG. 3 is a diagram representative of different concentrations of p-phenylenediamine (PPD) and the coagulation time obtained in the present method. The increase of PPD concentration affects the coagulation time of the agar gel. In the diagram, the 0 group is the control group without adding p-Phenylenediamine.

Referring to FIG. 3, with the increase in the concentration of p-phenylenediamine, the agar coagulation time is significantly longer and statistically significant. The data is expressed in mean±SEM for the triple test shown in FIG. 3. Data are represented as the mean±SEM; N=3○*p<0.05 compared with the control group; **p<0.01 compared with the control group.)

Figure 4:
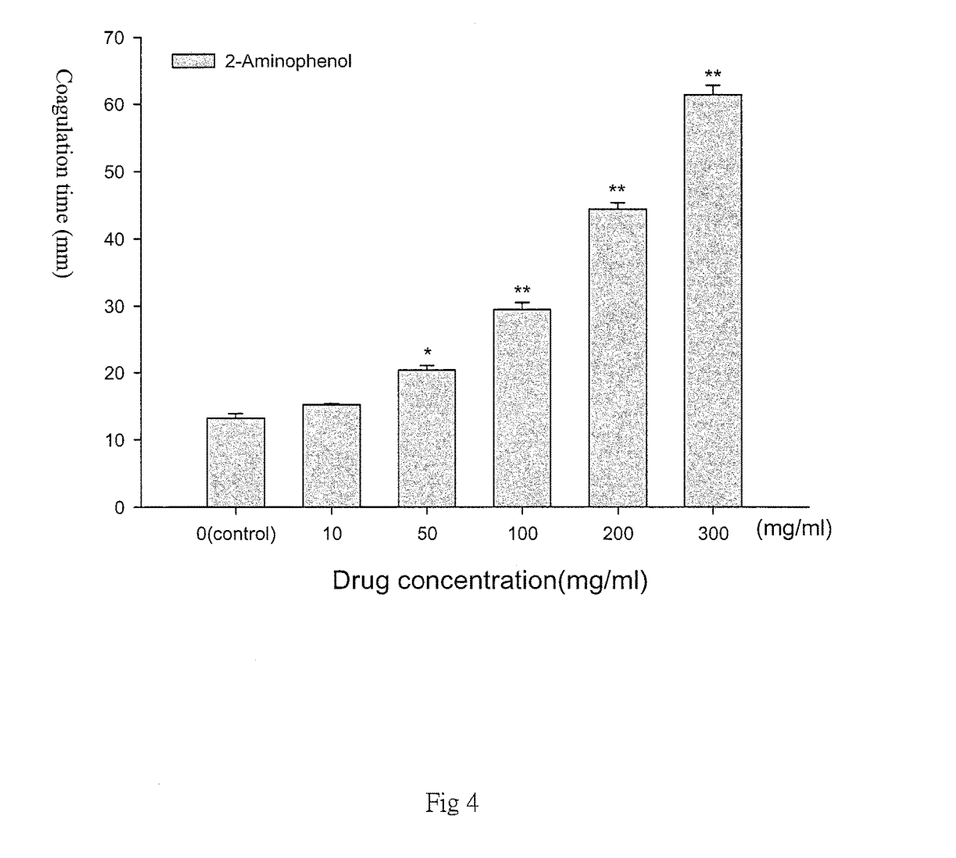
FIG. 4 is a diagram representative of different concentrations of 2-aminophenol (2-Aminophenol) and the coagulation time obtained in the present method. The increase in the concentration of 2-Aminophenol affects the agglomeration time of agar. In the diagram, the 0 group is the control group without adding 2-Aminophenol.

Referring to FIG. 4, with the increase in the concentration of 2-Aminophenol, the agar coagulation time is significantly longer and statistically significant; (the data is expressed in mean±SEM, where the triple test in FIG. 4; Data are represented as the mean±SEM; N=3○*p<0.05 compared with control; **p<0.01 compared with the control group.

Figure 5:
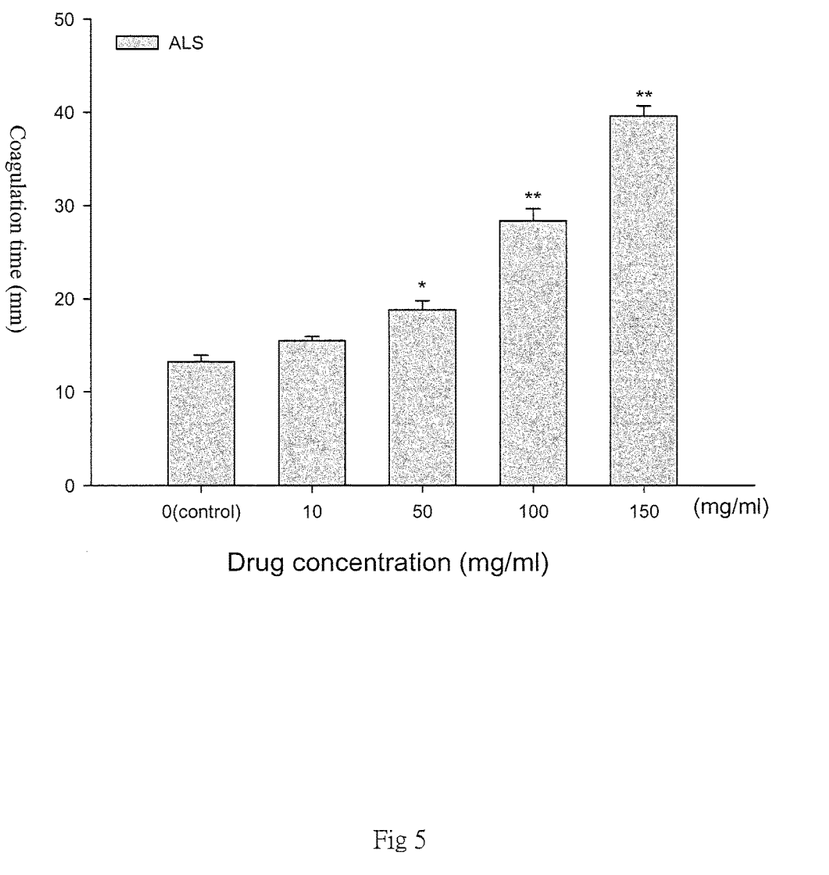
FIG. 5 is a diagram representative of different concentrations of Ammonium Lauryl Sulfate (ALS) and the coagulation time obtained in the present method. The increase of ALS concentration affects the agglomeration time of agar. In the diagram, the 0 group is the control group without adding ALS.

Referring to FIG. 5, with the increase in the concentration of Ammonium Lauryl Sulfate, the agar coagulation time is significantly longer and statistically significant. The data is expressed in mean±SEM for the triple test shown in FIG. 5. Data are represented as the mean f SEM; N=3○*p<0.05 compared with the control group; **p<0.01 compared with the control group.)

Figure 6:
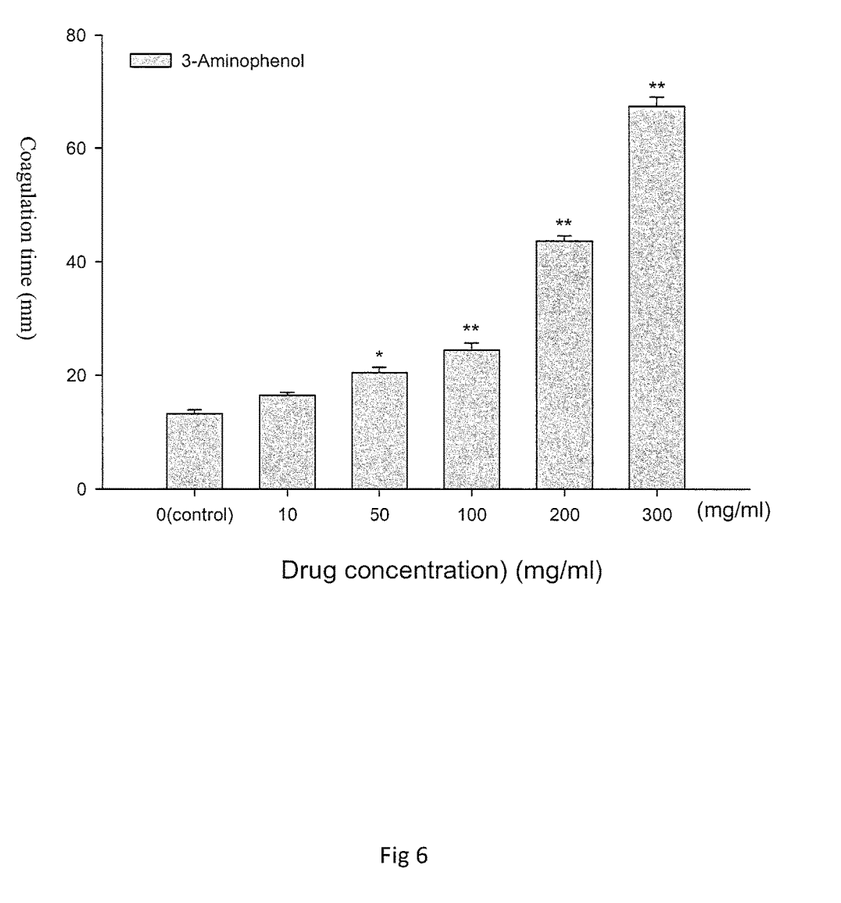
FIG. 6 is a diagram representative of the results of an analysis of the different concentrations of 3-aminophenol (3-Aminophenol) and coagulation time obtained in the present method. 3-Aminophenol concentration increased the agglomeration time of agar. In the diagram, the 0 group is the control group without adding 3-Aminophenol.

Referring to FIG. 6, with the increase in the concentration of 3-Aminophenol, the agar coagulation time is significantly longer and statistically significant. The data is expressed in mean±SEM for the triple test shown in FIG. 6. Data are represented as the mean f SEM; N=3○*p<0.05 compared with the control group; **p<0.01 compared with the control group.

In other words, the results presented in Table 2, Table 3, and FIGS. 2-6 show that the agar coagulation time and toxicity of the tested cosmetic materials are in a concentration-dependent relationship.

In summary, the agar coagulation time was measured with for samples under study and compared with the results of B16-F10 cells and 3T3 cytotoxicity. As shown in Tables 2 to 3, a higher toxic substance content of a sample under study corresponds to a longer agar coagulation time when compared to the control group.

In other words, the present invention was tested for agar coagulation time and compared with cell survival analysis experiments to verify that the cosmetic materials and samples are "not harmful to skin." The toxicity tests were performed for Butyl Paraben, Glycerin, Hydroxy Ethyl Cellulose, Lysine hydrochloride, Polyethylene Glycol, Polyquaternium-7, and Trisodium Citrate Dihydrate.

In addition, the present invention was tested to obtain the agar coagulation time to be compared with cell survival analysis experiments to verify the cosmetic materials and samples are "harmful to skin." The toxicity tests were performed for Ammonium Lauryl Sulfate, Disodium Lauroamphodiacetate, Hydrogen Peroxide, Methylchloroisothiazolinone, P-Methylaminophenol Sulfate, p-Phenylenediamine, Resorcinol, 2-Aminophenol, 3-Aminophenol, Sodium Sulfide-9-Hydrate, and Lactic acid.

Accordingly, the present invention provides a method for rapid determination of a toxic substance. In particular, The subject method determines whether a sample under study is toxic based on a plant agar coagulation time. The method can reduce the use of animals or cells experiments, not only for the purpose of protecting the animals, but also for reducing the cost of toxicity tests of drugs, food or cosmetics. The subject method rapidly and easily detects a toxic substance by agar curing in the time range of about 15 to about 60 minutes, in samples of cosmetics, food, drugs and other samples under study. The subject method is also applicable to determination whether various samples contain excessive toxic substances.

Although the present invention has been described in terms of specific embodiments and examples, the embodiments disclosed herein are for illustrative purposes only and various modifications and alterations might be made by those skilled in the art without departing from the spirit and scope of the invention as set forth in the following claims.

What is claimed is:

1. A rapid and simple method for determining toxic substances by plant gel agar coagulation, comprising the steps of:
   (1) preparing an agar and a sample under study, and heating the agar to complete dissolution to form a hot agar solution, wherein the agar concentration of the hot agar solution ranges between 1% and 6%, and wherein the volume in the hot agar solution ranges between 1 mL and 250 mL;
   (2) mixing the hot agar solution and the sample under study in a carrier to form a mixture;
   (3) cooling the mixture to a temperature ranging from a room temperature to 25° C. during a time duration till a predetermined cut-off time, wherein the time duration is a coagulation time, and wherein the cut-off time of the coagulation time is approximately 15 minutes to determine the cytotoxicity of the sample; and
   (4) categorizing the sample under study as a toxic substance if the coagulating time is greater than the cut-off time; and; and
   categorizing the sample under study as a non-toxic substance if the coagulation time is less than the cut-off time.

2. The method of claim 1, wherein the agar concentration in said mixture is 3%.

3. The method of claim 1, further comprising the step of:
   tilting the carrier at about 30°-60° from the vertical orientation.

4. The method of claim 1, wherein the volume of the mixture ranges from 100 mL to 200 mL.

5. The method of claim 1, wherein the toxic substance is defined as a substance causing damage to living cells.

6. The method of claim 1, wherein the sample under study is selected from a group including cosmetics, food products, or a medicine.

7. The method of claim 1, wherein the sample is selected from the group consisting of Ammonium Lauryl Sulfate, Butyl Paraben, Disodium Lauroamphodiacetate, Monoethanolamine, Glycerin, Hydrogen Peroxide, Methylchloroisothiazolinone Hydroxy Ethyl Cellulose, Lysine hydrochloride, p-hydroxybenzoate, Methylchloroisothiazolinone, Butylene Glycol, p-Methylaminophenol Sulfate, Polyethylene Glycol, Polyquaternium-7, p-Phenylenediamine, resorcinol, salicylic acid, 2-aminophenol, 3-aminophenol, Sodium sulfide-9-Hydrate, Squalane, Tocopherol Acetate, Trisodium Citrate Dihydrate, Isopropyl Myristate and Lactic acid, and a combination thereof.

* * * * *